US00PP37031P3

(12) United States Plant Patent
Boynton-Steele

(10) Patent No.: US PP37,031 P3
(45) Date of Patent: Oct. 14, 2025

(54) ***SALVIA* PLANT NAMED 'DH004'**

(50) Latin Name: *Salvia hybrida*
Varietal Denomination: DH004

(71) Applicant: Desert Honed LLC, Boise, ID (US)

(72) Inventor: Nicholas A. Boynton-Steele, Boise, ID (US)

(73) Assignee: Desert Honed LLC, Boise, ID (US)

( * ) Notice: Subject to any disclaimer, the term of this patent is extended or adjusted under 35 U.S.C. 154(b) by 0 days.

(21) Appl. No.: 19/037,279

(22) Filed: Jan. 26, 2025

(65) Prior Publication Data

US 2025/0248323 P1 Jul. 31, 2025

Related U.S. Application Data

(60) Provisional application No. 63/627,192, filed on Jan. 31, 2024.

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new *Salvia* plant designated 'DH004' particularly distinguished by violet blue flowers, a large leaf size; and a compact, low growing plant habit, is disclosed.

1 Drawing Sheet

CROSS REFERENCE TO RELATED MATTER

The present application claims priority to U.S. Application No. 63/627,192, as filed on Jan. 31, 2024, the entire contents of which is incorporated herein by reference for all purposes.

Genus and species: *Salvia hybrida.*
Variety denomination: 'DH004'.

BACKGROUND OF THE NEW PLANT 'DH004'

The present invention comprises a new and distinct variety of *Salvia*, botanically known as *Salvia hybrida*, and hereinafter referred to by the variety name 'DH004'. 'DH004' originated from a cross of the proprietary female *Salvia* plant '1431-6-T2' and the commercial male *Salvia* plant 'Calamity Jane' in April 2018 in Tucson, Arizona.

In fall of 2018 seeds were planted and a plant named 'DH004' was identified in the summer of 2019. 'DH004' was first vegetatively propagated by vegetative cuttings in Boise, Idaho. 'DH004' was found to reproduce true to type in successive generations of asexual propagation in Boise, Idaho via vegetative cuttings.

SUMMARY

The following are the most outstanding and distinguishing characteristics of 'DH004' when grown under normal horticultural practices in Boise, Idaho.

1. Violet blue flowers;
2. A large leaf size; and
3. A compact, low growing plant habit.

DESCRIPTION OF THE PHOTOGRAPHS

These new *Salvia* plants are illustrated by the accompanying photographs of plants grown in a greenhouse in Boise, Idaho. The colors shown are as true as can be reasonably obtained by conventional photographic procedures.

DESCRIPTION

Figure 1:
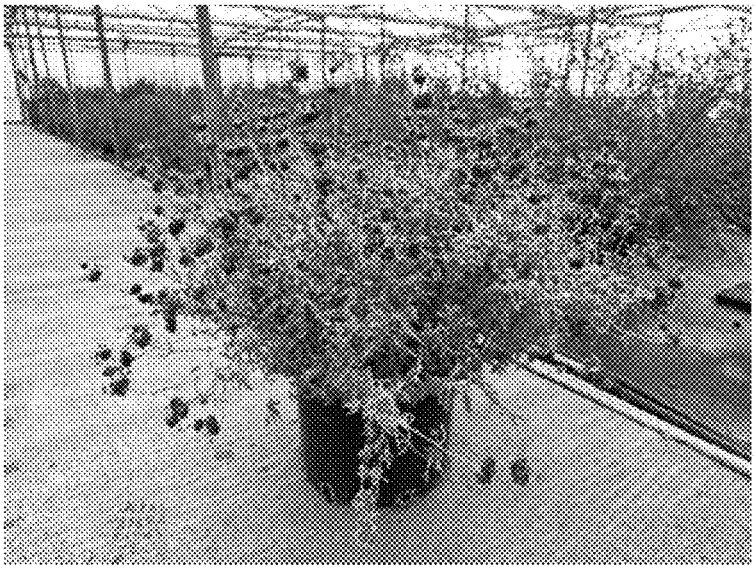
FIG. 1 is a whole plant photo of 'DH004' showing foliage, buds, and flowers. The photo is of a 4-year-old plant taken in December 2023 in Boise, Idaho.
Figure 2:
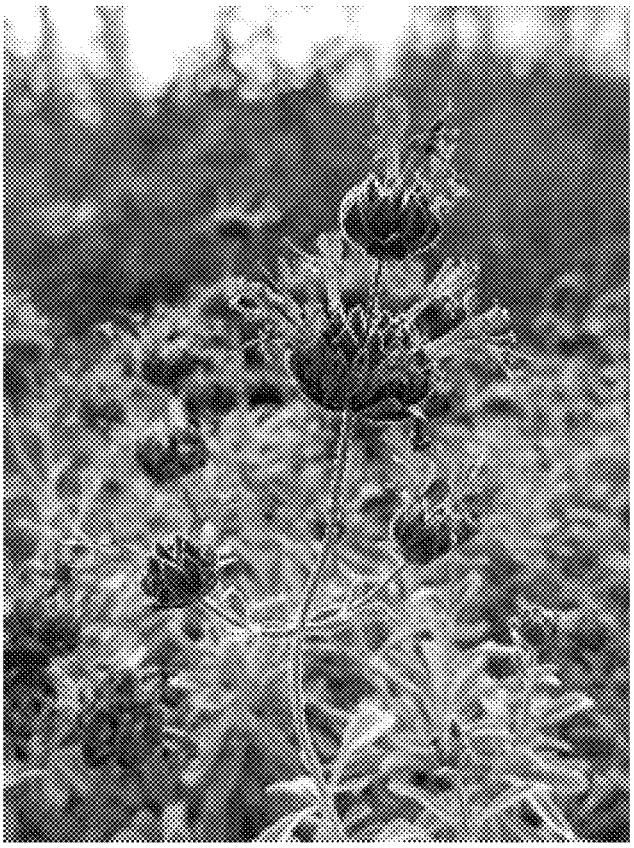
FIG. 2 is close-up photo of 'DH004' showing foliage, buds, and flowers. The photo is of a 4-year-old plant taken in December 2023 in Boise, Idaho.

The following detailed descriptions set forth the distinctive characteristics of 'DH004'. The data which define these characteristics were collected from asexual reproductions carried out in Boise, Idaho. Data was collected in January 2024 on 4 year old plants grown in a 7 gallon container is a plastic greenhouse. Color references are to The R.H.S. Colour Chart of The Royal Horticultural Society of London (R.H.S.), 4$^{th}$ edition (2001).

Classification:
*Family.*—Lamiaceae.
*Genus.*—*Salvia.*
*Species.*—*Hybrida.*
*Common name.*—Sage.

Parents:
*Female.*—*Salvia* plant '1431-6-T2' (unpatented).
*Male.*—*Salvia* 'Calamity Jane' (unpatented).

Plant:
*Propagation method.*—Cutting.
*Rooting system.*—Fibrous.
*Time to develop roots.*—2 to 3 weeks.
*Crop time.*—8 weeks for 1 gallon containers, 12 to 14 weeks for 3 to 5 gallon containers.
*Suggested container size.*—1 gallon, 3 to 5 gallon.
*Use.*—Home gardens, commercial landscapes, native gardens, waterwise gardens.

*Type*.—Perennial.
*Overall dimensions*.—50.0 cm to 75.0 cm tall by 100.0 cm to 130.0 cm wide.
*Cultural requirements*.—In ground, full to partial sun, infrequent deep watering, light shearing after main bloom season will keep the shrub compact. In containers, full sun, well drained media, consistently moist, pinched in plug stage, pinched at least once more for a one gallon, at least twice more for a 3 or 5 gallon.
*Hardiness*.—Zone 8a.
*Form*.—Low shrub.
*Growth habit*.—Compact, low-growing shrub.
*Blooming season*.—Late spring through midsummer.
*Lastingness of blooms*.—Each flower lasts 2 days, each inflorescence lasts 4-6 weeks.

Stems (below first pinch):
*Condition*.—Semi-ripe wood.
*Bark*.—Present at crown of plant, developing on lowest stems.
*Shape*.—Square becoming round with bark.
*Length*.—4.0 cm to 6.0 cm.
*Diameter*.—0.2 cm.
*Stem color* (*where exposed beneath bark*).—RHS 195C.
*Shape*.—Square in cross section.
*Texture*.—Smooth, tomentose.

Branches:
*Internode length*.—0.2 cm to 2.5 cm.
*Color*.—RHS 193B, RHS 192B and RHS 192C.
*Anthocyanin*.—Absent.

Leaves:
*Type, arrangement*.—Opposite.
*Attachment*.—Petiolate.
*Quantity per branch*.—12 to 30.
*Shape*.—Lanceolate to linear with a rounded apex.
*Length* (*mature*).—2.6 cm to 3.0 cm.
*Width* (*mature*).—0.7 cm to 1.0 cm.
*Margin*.—Entire to crenate.
*Thickness*.—0.1 cm.
*Surface* (*adaxial*).—Rugose, pubescent.
*Surface* (*abaxial*).—Net-veined, pubescent.
*Color* (*adaxial surface*).—Between RHS 190A and RHS 190C.
*Color* (*abaxial surface*).—Between RHS 190A and RHS 190C.
*Venation*.—Pinnate in pattern, recessed from upper surface, protruding from lower surface.
*Vein color*.—RHS 190D.
*Apex*.—Obtuse to rounded.
*Base*.—Strongly tapered to petiole.
*Fragrance*.—Musk, sweet.
*Stipules*.—Absent.

Petiole:
*Shape*.—"U" shaped near base to "D" shaped in cross section closer to the leaf blade.
*Length*.—0.6 cm to 1.1 cm.
*Width*.—0.15 cm.
*Texture*.—Pubescent.
*Color*.—RHS 190D.

Peduncle:
*Length* (*from uppermost leaf pair to base of lowest whorl of flowers*).—5.0 cm.
*Shape*.—Square in cross section.
*Width*.—0.2 cm.
*Texture*.—Slightly pubescent.
*Color*.—RHS 147C and RHS N77B and RHS N77C depending on sun exposure.

Inflorescence:
*Type*.—Paniculate verticillaster, 1 to 3 or more glomerules per stem.
*Flower arrangement*.—Opposite cyme.
*Length*.—8.0 cm to 15.0 cm.
*Width*.—4.0 cm to 5.0 cm.

Pedicel: Flowers are sessile.
*Bracts*.—Length: 1.2 cm to 1.4 cm long. Width: 0.5 cm to 0.8 cm. Shape: Ovate to elliptical, sometimes with a truncated base. Color is RHS N77A and N77C fading to RHS 147D at bract base.

Sepals: Fused into a tube.
*Quantity*.—Two upper and 2 lower sepals fused into a tube.
*Sepal length*.—1.2 cm.
*Sepal width*.—0.45 cm.
*Shape*.—Fused into tube, 3 acute points, two lower, one upper.
*Apex*.—Acute.
*Margin*.—Entire.
*Texture*.—Slightly tomentose.
*Color* (*both surfaces*).—RHS N77A and N77C fading to RHS 147D at bract base.

Flowers:
*Quantity*.—25 or more per glomerule.
*Aspect*.—Approximately 45 to 100 degrees in relation to peduncle.
*Shape*.—Tubular, opening to a bi-radially symmetric flower.
*Blooming period*.—Late fall through early summer in mild winter climates.
*Persistence*.—Individual flowers last two days, individual inflorescences last 4-6 weeks.
*Fragrance*.—None (perhaps the fragrance of the foliage overwhelms any fragrance).

Bud:
*Shape*.—Tube shaped with a rounded end.
*Dimensions* (*immediately before petal emergence*).—Length: 1.2 cm. Diameter: 0.3 cm to 0.4 cm.
*Color*.—RHS 147D.
*Surface*.—Smooth.

Corolla:
*Shape*.—Tubular, opening to a bi-radially symmetric flower with 5 petals.
*Length*.—2.0 cm.
*Width*.—Tube 0.2 cm.
*Texture*.—Smooth.
*Color* (*both surfaces*).—RHS N89A and N89B, fading to RHS 91D at base of tube.

Petals:
*Quantity*.—5.
*Arrangement*.—Biradially symmetric.
*Upper petal*.—2. Shape: Ovate. Length: 0.5 cm with a 0.2 cm sinus lobe. Width: 0.15 cm. Texture: Adaxial surface: Smooth. Abaxial surface: Smooth. Apex: Rounded. Base: Fused to tube. Margin: Entire. Color (both surface): RHS N89A and N89B.
*Lower petal, lip*.—Shape: 0.4 cm long, two lobed, each lobe 0.1 cm wide, 0.1 cm long. Length: 0.4 cm. Width: 0.3 cm. Texture (both surfaces): Smooth. Apex: Rounded. Base: Fused to tube. Color (both surfaces): RHS N89A and N89B.

*Lower petal, lateral lobes*.—Shape: Rounded. Length (each lateral lobe): 0.3 cm. Width: 0.2 cm. Texture: Adaxial surface: Smooth. Abaxial surface: Smooth. Apex: Rounded. Base: Fused. Margin: Entire. Color (both surfaces): RHS N89A and N89B.

Reproductive organs:

*Stamens*.—Quantity: 2. Filaments: Length: 1.4 cm. Color: RHS 91D.

*Anthers*.—Attachment, shape: Basifixed. Length: 0.2 cm. Width: 0.5 cm to 0.1 cm. Color: RHS 11C.

*Pollen*.—Amount: Medium. Color: RHS 11C.

*Pistil*.—Quantity: 1. Style: Length: 1.7 cm. Diameter: 0.5 cm. Color: RHS 86A at apex (stigma), RHS 85A on style. Stigma: Shape: Forked. Length: 0.05 cm to 0.1 cm. Diameter: 0.15 cm.

*Ovary*.—Shape: Cylindrical. Length: 0.1 cm. Diameter: 0.1 cm. Color: RHS 199D and RHSC.

Disease and pest susceptibility: Occasional Powdery Mildew. Occasional *Pithium* or other water mold susceptibility in water-logged or poorly drained soil.

COMPARISON OF 'DH004' WITH PARENTAL LINES AND KNOWN VARIETY

'DH004' is distinguished from the female parent as described in Table 1 and the male parent as described in Table 2.

TABLE 1

Comparison with Female Parental Line

| Trait | Variety 'DH004' | Female parent S. '1431-6-T2' |
|---|---|---|
| Leaf size | 2.6 cm to 3.0 cm × 1.0 cm | 2.2 cm × 0.8 cm |

TABLE 1-continued

Comparison with Female Parental Line

| Trait | Variety 'DH004' | Female parent S. '1431-6-T2' |
|---|---|---|
| Flower color | RHS N89A and RHS N89B | RHS N88A and RHS N87A |

TABLE 2

Comparison with Male Parental Line

| Trait | Variety 'DH004' | Male Parent 'Calamity Jane' |
|---|---|---|
| Flower color | Violet blue (RHS N89A and RHS N89B) | Pale, grey-white |

'DH004' can be compared to the commercial *Salvia* variety 'Celestial Blue' (unpatented). Differences between the varieties are described in Table 3.

TABLE 3

Comparison with Similar Variety

| Trait | Variety 'DH004' | 'Celestial Blue' |
|---|---|---|
| Blooming season | November to April in zones 9-10 | Typically blooms May to July in zones 9-10 |

I claim:

1. A new and distinct cultivar of *Salvia* Plant Named 'DH004' as shown and described herein.

* * * * *